United States Patent [19]
Ryan et al.

[11] Patent Number: 6,066,139
[45] Date of Patent: May 23, 2000

[54] APPARATUS AND METHOD FOR STERILIZATION AND EMBOLIZATION

[75] Inventors: Thomas Patrick Ryan, Fort Collins, Colo.; Gregory Herbert Lambrecht, Cos Cob, Conn.

[73] Assignee: Sherwood Services AG, Schaffhausen, Switzerland

[21] Appl. No.: 08/649,146

[22] Filed: May 14, 1996

[51] Int. Cl.⁷ .................................................. A61B 17/36
[52] U.S. Cl. ............................... 606/50; 606/40; 606/41; 606/135
[58] Field of Search ............................ 606/31–34, 37–42, 606/45–50, 135; 607/100, 101; 128/898

[56] References Cited

U.S. PATENT DOCUMENTS

| | | | |
|---|---|---|---|
| Re. 33,925 | 5/1992 | Bales et al. ................................ | 606/48 |
| 3,800,800 | 4/1974 | Garbe et al. . | |
| 3,840,016 | 10/1974 | Lindemann . | |
| 3,858,586 | 1/1975 | Lessen . | |
| 4,057,063 | 11/1977 | Gieles et al. . | |
| 4,411,266 | 10/1983 | Cosman . | |
| 4,587,975 | 5/1986 | Salo et al. . | |
| 4,685,459 | 8/1987 | Koch et al. . | |
| 4,700,701 | 10/1987 | Montaldi . | |
| 4,966,597 | 10/1990 | Cosman ..................................... | 606/50 |
| 4,989,601 | 2/1991 | Marchosky et al. . | |
| 5,095,917 | 3/1992 | Vancaillie . | |
| 5,122,137 | 6/1992 | Lennox . | |
| 5,147,353 | 9/1992 | Everett . | |
| 5,151,100 | 9/1992 | Abele et al. . | |
| 5,167,660 | 12/1992 | Altendorf ................................... | 606/40 |
| 5,178,620 | 1/1993 | Eggers et al. ............................. | 606/41 |
| 5,242,390 | 9/1993 | Goldrath . | |
| 5,303,719 | 4/1994 | Wilk et al. . | |

(List continued on next page.)

Primary Examiner—Linda C. M. Dvorak
Assistant Examiner—Bryan K. Yarnell

[57] ABSTRACT

An apparatus for transcervical sterilization or transcatheter embolization with a controlled bipolar RF catheter for creating thermal lesions in the fallopian tubes or thrombosing vessels has a catheter elongate along an axis thereof with a patient end. The catheter is circular and sized for transcervical insertion into the fallopian tube or transcatheter vessel insertion, respectively. A connector on an end of the catheter opposite the patient end has the terminations for RF and monitoring and is shaped for the surgeon to manipulate during placement and withdrawal. Two or more bipolar electrodes on the patient end are placed so each electrode is spaced from another with each circumscribing the catheter. A mucosa or thrombus sensor responsive to applied RF energy passing between the two or more bipolar electrodes determines the condition of the transmural formation of a lesion or the thrombus between each of the electrodes. The sensor is a temperature sensor positioned in the space between the electrodes measures the change in mucosal layer temperature or the thrombus during the application of RF energy. An RF generator electrically coupled to the electrodes and the sensor is alternately a phase detector in circuit with the coupling determines reactance of tissue as an indicator of lag or lead of the voltage wave form or current wave form delivered or is an impedance responsive circuit positioned in the RF generator to determine voltage and current delivered so a calculator finds impedance delivered for finding initial electrode contact with the tissue and for measuring the change in mucosal layer. The temperature sensor connects to an RF generator with control circuitry regulating delivery to a temperature range. A method for sterilization has the steps of inserting a catheter, delivering RF and monitoring the effect on the mucosa or thrombus, circumscribing the catheter with two or more bipolar electrodes, each of the electrodes spaced from one another and passing RF energy therebetween.

24 Claims, 8 Drawing Sheets

U.S. PATENT DOCUMENTS

| | | |
|---|---|---|
| 5,336,222 | 8/1994 | Durgin, Jr. et al. . |
| 5,348,554 | 9/1994 | Imran et al. . |
| 5,405,346 | 4/1995 | Grundy et al. . |
| 5,422,567 | 6/1995 | Matsunaga ................ 606/38 |
| 5,423,811 | 6/1995 | Imran et al. . |
| 5,486,161 | 1/1996 | Lax et al. . |
| 5,496,312 | 3/1996 | Klicek ................ 606/50 |
| 5,499,981 | 3/1996 | Kordis . |
| 5,514,129 | 5/1996 | Smith ................ 606/40 |
| 5,522,815 | 6/1996 | Durgin, Jr. et al. . |
| 5,527,279 | 6/1996 | Imran ................ 606/41 |
| 5,540,679 | 7/1996 | Fram et al. . |
| 5,540,681 | 7/1996 | Strul et al. ................ 606/34 |
| 5,545,161 | 8/1996 | Imran . |
| 5,545,193 | 8/1996 | Fleischman et al. . |
| 5,556,396 | 9/1996 | Cohen et al. . |
| 5,558,073 | 9/1996 | Pomeranz et al. . |
| 5,573,533 | 11/1996 | Strul . |
| 5,582,609 | 12/1996 | Swanson et al. . |
| 5,626,576 | 5/1997 | Janssen . |
| 5,658,278 | 8/1997 | Imran et al. . |
| 5,673,695 | 10/1997 | McGee et al. . |
| 5,687,723 | 11/1997 | Avitall ................ 606/41 |
| 5,697,927 | 12/1997 | Imran et al. . |

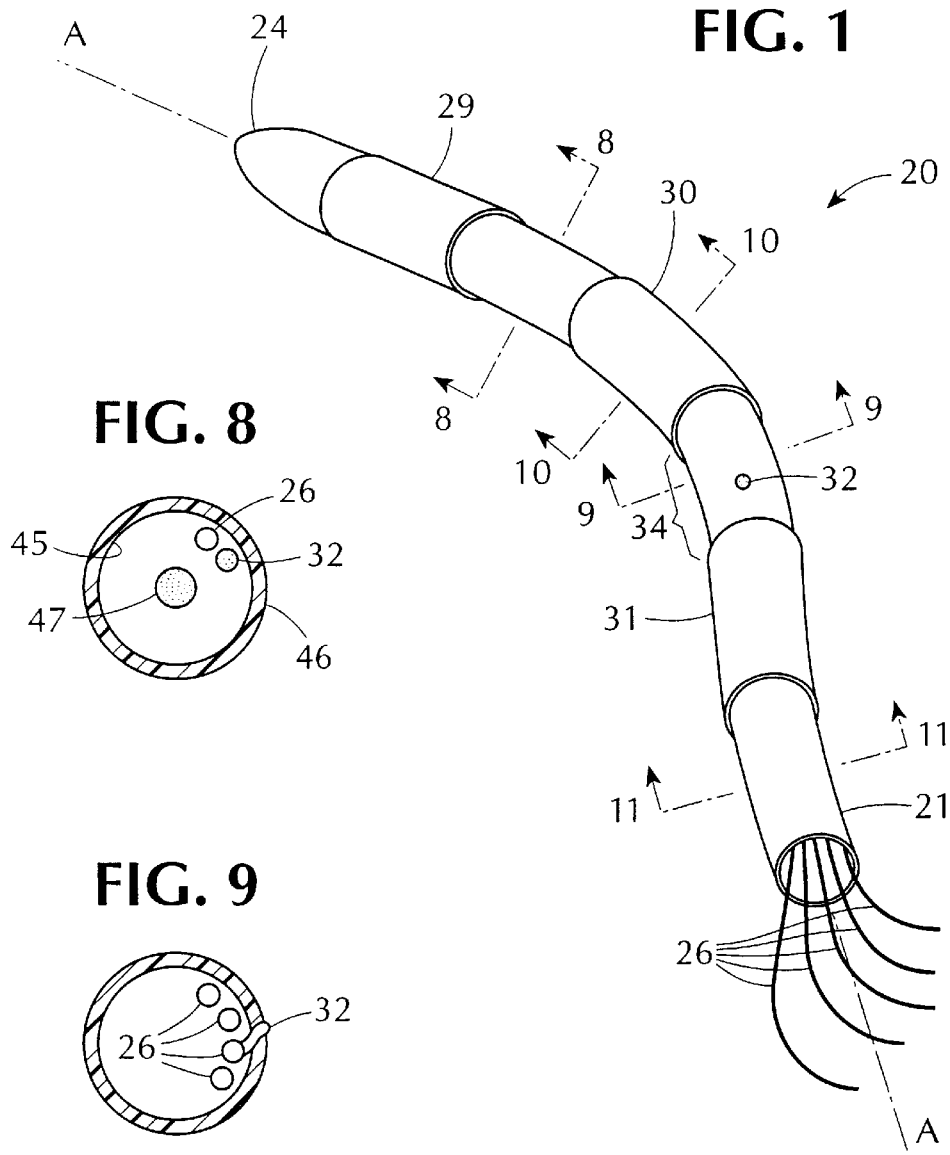
FIG. 1
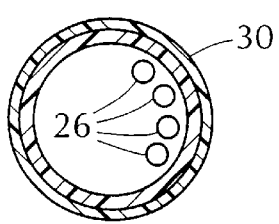
FIG. 8
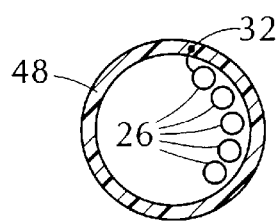
FIG. 9
FIG. 10
FIG. 11

APPARATUS AND METHOD FOR STERILIZATION AND EMBOLIZATION

1. FIELD OF THE INVENTION

This relates to an apparatus and method for transcervical sterilization and transcatheter embolization. More particularly, a temperature controlled bipolar RF catheter and its use for creating thermal lesions in the fallopian tubes or thrombus in a vessel, respectively.

2. BACKGROUND OF THE DISCLOSURE

U.S. Pat. No. 3,840,016 has an electrocoagulation device for intrauterine sterilization of the fallopian tube using a monopolar electrode and temperature control of just the electrode. U.S. Pat. No. 4,057,063 has a monopolar catheter to treat the fallopian tubes with impedance increase monitoring to assess the completion of treatment.

U.S. Pat. No. 4,411,266 is an RF lesioning electrode with temperature sensor in the conductive tip. The system is monopolar. U.S. Pat. No. 5,486,161 is an RF probe with heating through a hollow needle tip in monopolar fashion. U.S. Pat. No. 4,057,063 senses impedance of tissue in the vicinity of a monopolar electrode with a 5 second activation at 4.8 W with no control to lesion the entry from uterus to fallopian tubes.

U.S. Pat. No. 5,122,137 has a monopolar RF electrode with a temperature sensor buried therein. Circuitry measures temperature when the RF power is off. This electrode is used to thermally occlude the fallopian tubes.

U.S. Pat. No. 5,303,719 includes a delivery system for laser, electrical power or adhesive to the fallopian tubes. The electrical modality is monopolar.

U.S. Pat. No. 4,685,459 has bipolar forceps with temperature sensors on the electrodes to limit the maximum temperature of the tissue contacted during RF coagulation. U.S. Pat. No. 4,685,459 is a bipolar forceps device with power controlled to the faces by buried thermal probes in the faces of the opposing forceps ends.

U.S. Pat. No. 4,700,701 is an electrically energized cautery of the fallopian tube followed by insertion of a plug. U.S. Pat. No. 5,095,917 has a bipolar RF catheter to lesion superficially the mucosa layer near the uterotubal junction before a porous plug is inserted and there is no control of power and no monitoring during RF activation. U.S. Pat. No. 5,303,719 destroys the inner layer of cells in fallopian tube and then uses suction to collapse and adhere the walls but there is no mention of RF energy of control.

U.S. Pat. No. 4,587,975 has an angioplasty catheter with cylindrical electrodes used for recording impedance plethysmography. A thermal cautery probe for blood vessels with a resistive heater does not have RF. It is temperature controlled by using a diode breakdown voltage. U.S. Pat. No. 5,122,137 concentrates current in the vicinity of an electrode which must be thermally conductive due to the thermocouple buried inside herein a multiple electrode configuration has each electrode sensed.

Female sterilization for the prevention of pregnancy may be a necessary procedure performed laparoscopically with electrosurgery. Typically, the fallopian tubes are grasped with bipolar forceps on the outside of the tube and electrosurgical energy is applied over a period of time until the surgeon sees the tubes coagulate. Following this, a second and third coagulation made on either side of the original extend the length of the coagulation.

Several papers, published since 1878, disclose procedures that attempt to use heat to close the fallopian tubes. A hot probe cauterized the opening of the fallopian tube from the uterus (tubal osteum). Later techniques with uncontrolled monopolar RF energy delivery sometimes failed. The use of a bipolar probe followed by placement of a plug in uterine opening of the fallopian tube had no control of power and an uninsulated tip of 1.5 mm length, thus operating at the edge of the fallopian tube and not farther inside the tube.

Sterilization requires certainty with respect to the apparatus and the procedure used. The background herein discusses devices which fail to provide a level of certainty because the idea for each of the identified prior techniques and instruments was to seal the fallopian tubes with the treatment. The less invasive approach disclosed herein recognizes that natural healing will produce a superior, reliable, atraumatic and consistent result not found in the prior patents or literature.

Another use for this bipolar RF catheter device is for controlled use in blood vessels for embolotherapy. This would include sealing of arterial feeder vessels that communicate with tumors in order to reduce the blood supply to the tumor either prior to surgery or as a treatment to necrose the tumor. In cases where congenitally formed vessels are anomalous, these would be sealed off by this catheter device. In the lung, anomalous vessels shunt blood flow and need to be closed. Arterovenous fistulas, pseudoaneurysms caused by trauma or infection, hepatic artery-bile duct fistulas or sites of active hemorrhage are also applications for this device. In all of these examples, the application of RF energy will thrombose and occlude the vessel by heating the blood and the vessel wall to provide closure or sealing. Symptomatic arterovenous malformations in the uterus is often treated by hysterectomy since it otherwise results in massive vaginal bleeding and spontaneous abortions. Embolization can prevent these outcomes. Massive vascular hemorrhage can result in multi-organ failure. Many of these patients are not candidates for surgery.

Several methods have been tried to occlude vessels. These include placing polyvinyl alcohol particles or metal flakes, degradable starch, cyanoacrylate, ethanol, detachable balloons, small coils or gelatin sponges. These techniques all deal with a foreign body left behind with potential to migrate or flow out of the intended site. Recanalization can also result with some of these techniques. Precise control of coils during positioning or withdrawal is often challenging. Non-target tissue embolization results in tissue devitalization of normal structures. The only techniques described in the medical literature for thermal embolization are the use of iron microspheres which are heated in an external radiofrequency field at 100 kHz. Another technique was to use hot contrast agents, as used in angiography, heated to 100 C. Yet another technique used a laser with a metal cap to thrombose with heat and then leave the metal cap permanently in place.

U.S. Pat. No. 5,053,006 discusses permanent occlusion of arteries using a laser. The technique involves injecting a dye into the vessel and then introducing laser light at a wavelength to perform photochemical injury to the vascular endothelium. U.S. Pat. No. 5,108,407 suggests placing a coil for embolization connected to a fiberoptic cable. Laser energy is introduced into the cable to melt the adhesive and release the coil. U.S. Pat. No. 5,354,295 also involves a coil placed for endovascular occlusion. The coil is then heated by flowing current between the electrode and the tip. Energy is activated until the wire disconnects from the coil. There is no mention of RF energy and the unit is not bipolar.

U.S. Pat. No. 5,405,322 uses a balloon to heat the wall of an aneurysm. RF current flows between the electrodes to heat the fluid in the balloon which then heats tissue through thermal conduction. There is no RF energy flowing through tissue. U.S. Pat. No. 5,437,664 is a device for occluding the lumen of veins. The electrode is energized in a monopolar fashion and may utilize impedance or temperature to signal the end of the treatment. No temperature of impedance endpoints are suggested. There is no control of power but only shutoff when endpoints are achieved.

The device described here will embolize by inserting the device into the vessel and precisely applying radiofrequency energy to heat the blood in the vessel to a controlled temperature for thrombosis and sealing of the vessel to occur. This autologous clot will not cause any foreign body reaction since nothing is left behind after the removal of the catheter.

SUMMARY OF THE INVENTION

To simplify this procedure and obviate surgery, an apparatus and clinical method have been developed that takes advantage of transcervical access and lesioning from inside of the fallopian tube in a minimally invasive and controlled fashion that is not traumatic.

An apparatus for transcervical sterilization with a controlled bipolar RF catheter for creating thermal lesions in the fallopian tubes may have a catheter elongate along an axis thereof and with a patient end. The catheter is preferably generally circular in cross section and sized for transcervical insertion into the fallopian tube. A connector on the end of the catheter opposite the patient end may include the terminations for RF and monitoring. The connector can be shaped for the surgeon to manipulate during transcervical placement and withdrawal. Two or more bipolar electrodes on the patient end of the catheter may be placed so each electrode is preferably spaced from one another with each of the electrodes circumscribing the catheter. A mucosa sensor responsive to applied RF energy passing between the two or more bipolar electrodes preferably determines the condition of the transmural formation of a lesion between each of the electrodes.

The mucosa sensor is in the preferred embodiment a temperature sensor positioned on the patient end in the space between the two or more bipolar electrodes for measuring the change in mucosal layer temperature during the application of RF energy. An RF generator could be electrically coupled to the two or more bipolar electrodes and the mucosa sensor is in this approach a phase detector positioned in the RF generator in circuit with the electrical coupling between the RF generator and the two or more bipolar electrodes for determining reactance of tissue as an indicator of lag or lead of the voltage wave form or current wave form delivered to the patient end for measuring the change in mucosal layer as a tissue effect endpoint during the application of RF energy. An RF generator is electrically coupled to the two or more bipolar electrodes when the mucosa sensor is an impedance responsive circuit positioned in the RF generator. The impedance responsive circuit in the electrical coupling between the RF generator and the two or more bipolar electrodes may determine voltage and current delivered and a calculator in the impedance responsive circuit for finding impedance delivered to the patient end for finding initial electrode contact with the tissue and for measuring the change in mucosal layer during the application of RF energy.

In an embodiment there may be three electrodes connected to an RF generator to deliver RF energy selectively between one pair of electrodes at one time to create a plurality of lesions therebetween inside the mucosal layer of the fallopian tubes. The catheter is most preferably flexible and might include a blunt tip at the patient end to facilitate introduction into the fallopian tubes and to avoid perforation thereof. The temperature sensor could be connected to an RF generator that has energy delivery control circuitry to regulate delivery of RF to a temperature range of about 95 C. to 105 C. between the electrodes. The energy delivery control circuitry may include a proportional controller for substantially regulating the RF energy delivery to control temperature rise time for lesion formation and to maintain the temperature near the mid point of a temperature range during thermal necrosis of tissue for the transmural formation of a lesion.

A videoscope could surround the transcervically inserted catheter for the visualization of the progression of the lesion via video. The temperature sensors are preferably located centrally relative to the axis within the space between adjacent electrodes. The circular cross section of the catheter can be solid with the temperature sensors located at the center of the solid circular cross section of the catheter. The circular cross section of the catheter might be hollow having an inside and a outside wall of the catheter. The temperature sensors are then preferably located on the inside wall. The temperature sensors alternatively can be located on the outside wall. The temperature sensors alternatively can be located in the catheter wall.

The calculator may include a memory including an equation for the power delivery with respect to time and a comparator in the calculator to compare power delivered to power required by the equation for closed loop control of the power delivered over elapsed time to shape lesion spread and shape. The one or more bipolar electrodes are preferably spaced apart to create multiple separate lesions inside the fallopian tube without moving the placed catheter. The one or more electrodes are possibly of different sizes so that when tissue contact is made the position near one of the electrodes is defined and the extent, depth and severity of the lesion formation preferred results. The equation in the memory preferably controls power to reduce sticking and charring to the electrode of tissue in contact therewith.

A method for transcervical sterilization with thermal energy delivery for creating lesions in the fallopian tubes may have steps including transcervically inserting into a fallopian tube a catheter elongate along an axis thereof and with a patient end, the catheter generally circular in cross section and sized for the fallopian tube. The step of delivering RF and monitoring the effect of RF on the mucosa at a connector on the end of the catheter opposite the patient end may be included. Circumscribing the catheter with two or more bipolar electrodes on the patient end of the catheter, each of the electrodes spaced from one another and passing RF energy between the two or more bipolar electrodes are steps. The step of determining the condition of the transmural formation of a lesion between each of the electrodes with a mucosa sensor located between the electrodes is then followed.

The method step of transcervically inserting into a fallopian tube might be performed by the surgeon manipulating during transcervical placement and withdrawal the connector shaped and located at the end opposite. The step of determining the condition of the transmural formation of a lesion between each of the electrodes may include measuring impedance change during delivery of RF. The step of determining the condition of the transmural formation of a lesion between each of the electrodes could include measuring temperature change during delivery of RF. The step of determining the condition of the transmural formation of a lesion between each of the electrodes may include controlling temperature of the mucosa during delivery of RF to the range of about 95 C. to 105 C. The step of controlling temperature of the mucosa during delivery of RF can include formation of a lesion substantially through the wall of the fallopian tube. The step of collapsing the lesioned surface of the fallopian tube after withdrawal of the catheter followed by adhering with fibrosis the collapsed adjoining surfaces during a period of three to ten days after withdrawal is preferably followed.

An apparatus for transcervical sterilization with thermal energy delivery for creating lesions in the fallopian tubes may include an elongate circular catheter with a patient end sized for transcervical insertion into the fallopian tube. One or more piezoelectric transducers are preferably on the patient end of the catheter so each piezoelectric transducer is a thermal energy source, each piezotransducer is a thin cylinder circumscribing the catheter and each piezotransducer is located to heat mucosa tissue. A connector on the end of the catheter opposite the patient end can include the terminations for piezoelectric energy and monitoring with the connector shaped for the surgeon to manipulate during transcervical placement and withdrawal. A mucosa sensor responsive to applied thermal energy passing from the one or more piezotransducers determines the condition of the transmural formation of a lesion about the one or more piezotransducers. The one or more piezotransducers are preferably spaced axially from at least one adjacent piezotransducer.

Safe, effective, inexpensive minimally invasive method of transcervical tubal sterilization could have a major impact on women's health. Unlike devices that include the insertion of a plug either with or without deposition of energy, the apparatus leaves no foreign body in place after the lesion is created. Some techniques such as the mixing and application of an adhesive require a high degree of user skill and require the introduction of foreign material to the reproductive tract. Some devices endeavor to destroy cells along the inner surface of the fallopian tubes while the device disclosed herein aims for limiting to intramural cell destruction. The frequency of RF ablation is maintained above 200 kHz to avoid muscle or nerve stimulation.

Another major use of this device would be in transcatheter embolotherapy. This therapy is done by passing a catheter into a blood vessel and occluding the vessel by creating a thrombus to stop blood flow. This requires a flexible catheter with a hollow center for over-the-wire techniques.

BRIEF DESCRIPTION OF THE DRAWINGS

FIG. 1 is a perspective view of an apparatus for transcervical sterilization with a controlled bipolar RF catheter for creating thermal lesions in the fallopian tubes illustrated before insertion.

FIG. 8 is a cross section taken along line 8—8 in FIG. 1 of the gap between electrodes.

FIG. 9 is a cross section taken along line 9—9 in FIG. 1 of the location of the sensor.

FIG. 10 is a cross section taken along line 10—10 in FIG. 1 of the electrode on the catheter.

FIG. 11 is a cross section taken along line 11—11 in FIG. 1 of the sensor in the catheter wall.

DETAILED DESCRIPTION OF THE INVENTION

Figure 3:
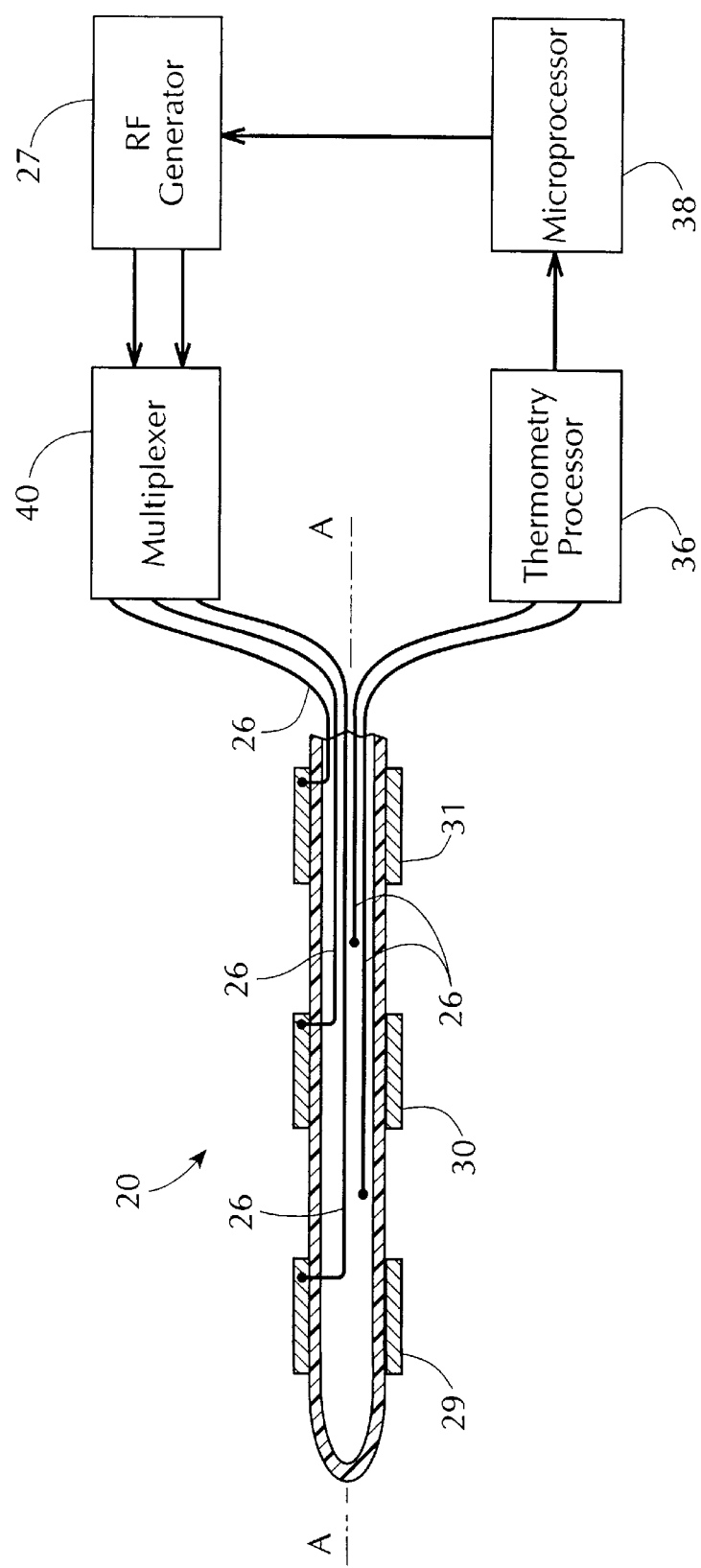
FIG. 3 is a schematic diagram of the coupling to the lesioning electrodes with the RF generator and the sensor responsive circuitry to control the lesion shape and extent.
Figure 4:
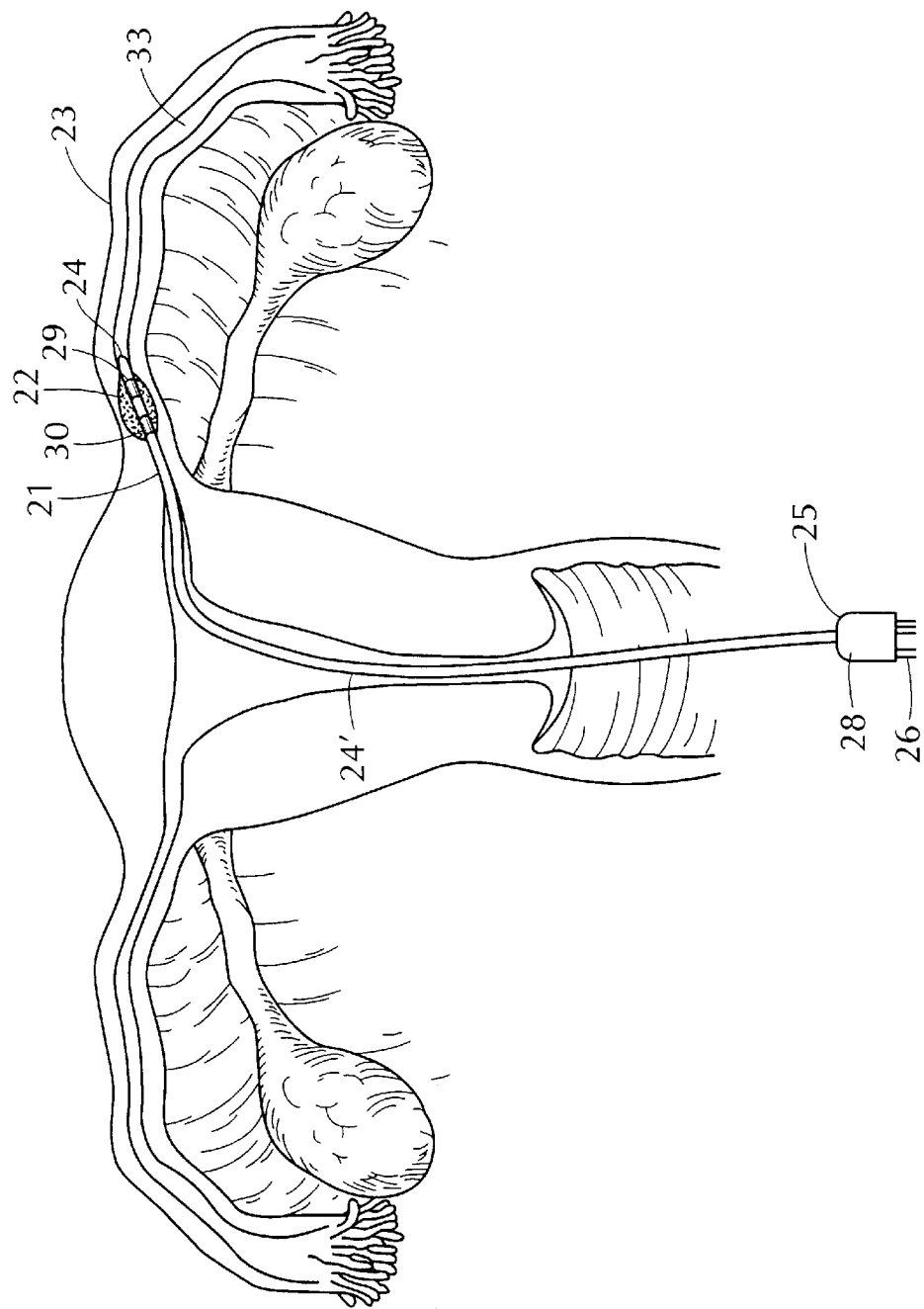
FIG. 4 is the transcervically inserted apparatus having the patient end in the fallopian tube with the accompanying lesion passing transmurally.
Figure 5:
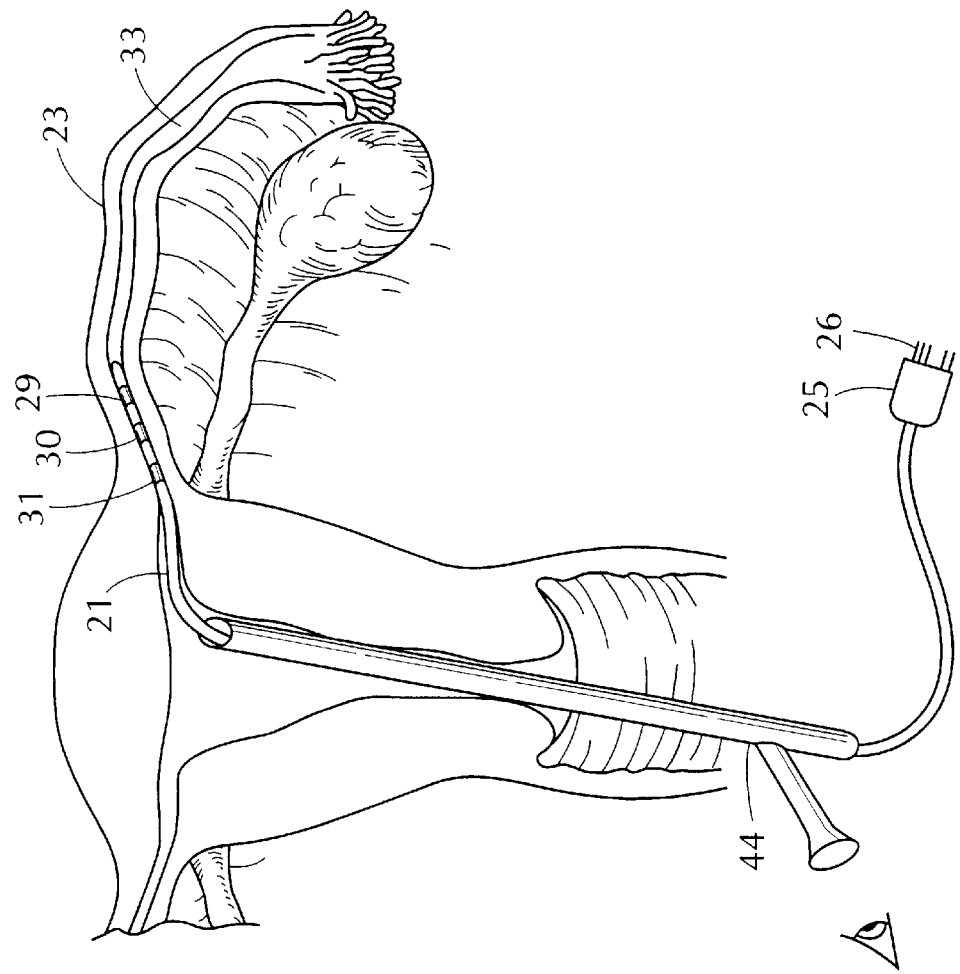
FIG. 5 is the apparatus transcervically inserted through the operating channel of a hysteroscope with the patient end observable entering the fallopian tube.
Figure 6:
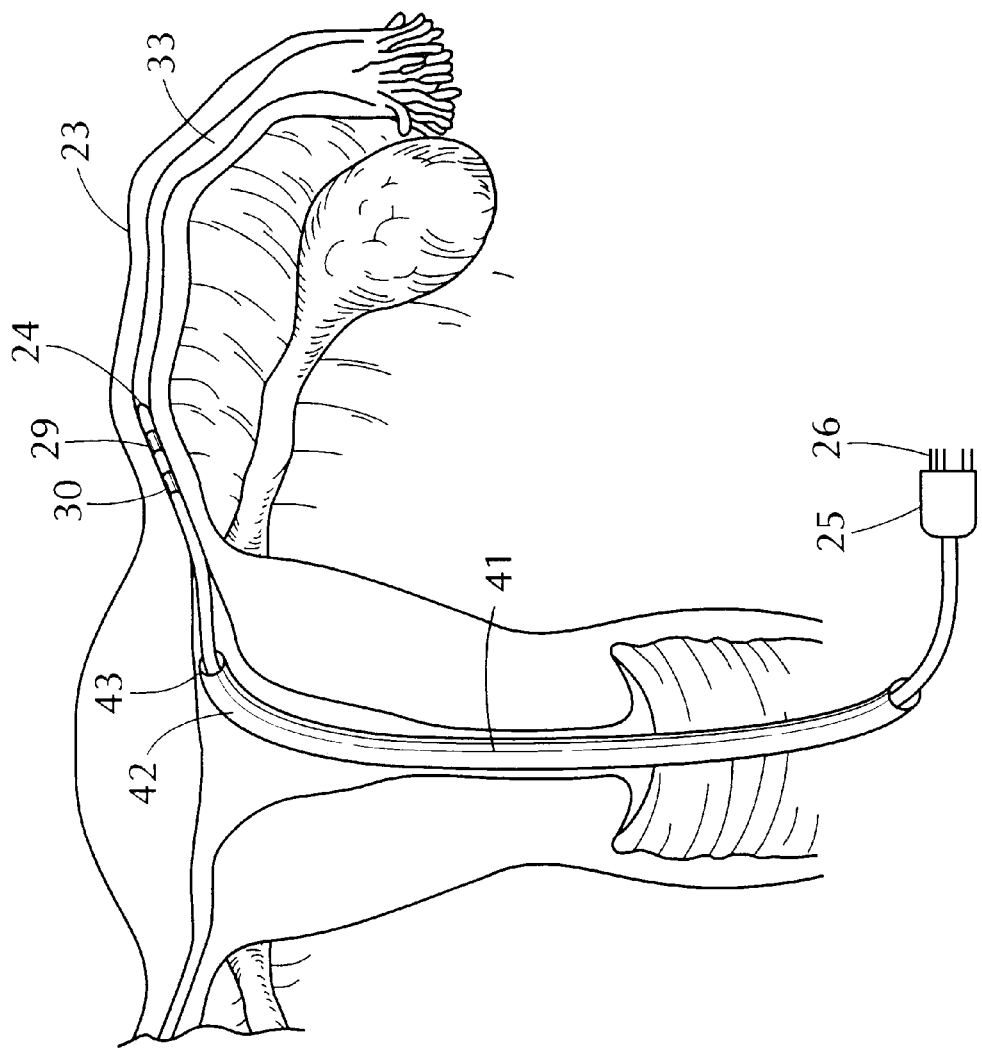
FIG. 6 is the apparatus inserted through a prebent transcervical introducer tube exiting at the tubual ostium for entering the fallopian tube with the patient end of the apparatus.

An apparatus 20 for transcervical sterilization with a controlled bipolar RF catheter 21 for creating thermal lesions 22 in the fallopian tubes 23 shown in FIGS. 1, 4, 5, 6 and 7 has the catheter 20 elongate along an axis "A" thereof and with a patient end 24. The catheter 21 is generally circular in cross section and sized for transcervical insertion into the fallopian tube as shown in FIGS. 4, 5, and 6. A connector 25 on the end of the catheter 21 opposite the patient end 24 includes the wires and terminations 26 for connection to an electrosurgical generator 27 shown in FIG. 3 that supplies RF and controls the amount by monitoring. The connector 25 can be shaped like a handle 28 in FIG. 4 for the surgeon to manipulate during transcervical placement and withdrawal. Two or more bipolar electrodes 29, 30 and 31 on the patient end 24 of the catheter 21 are placed so each bipolar electrode 29, 30 or 31 is preferably spaced from each other with each of the bipolar electrodes 29, 30 or 31 circumscribing the catheter 21 as shown in FIGS. 1, 3, 5, 6 and 7. The catheter 21 patient end 24 is flexible and a central part 24' of the catheter 21 between the patient end 24 and the connector 25 may be less flexible than the patient end 24 to aid in insertion through collapsed or circuitous vasculature as in FIG. 7.

Figure 13:
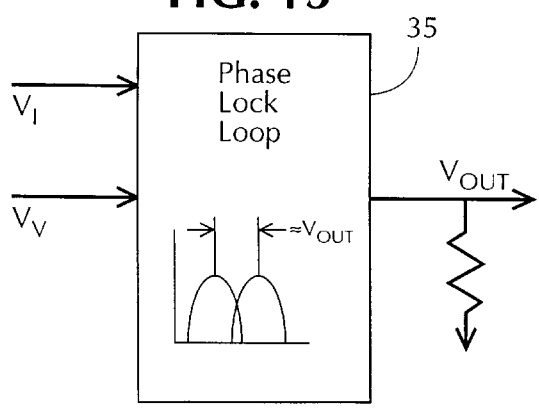
FIG. 13 is a schematic diagram of a phase detection circuit used for the control of the application of RF energy.
Figure 12:
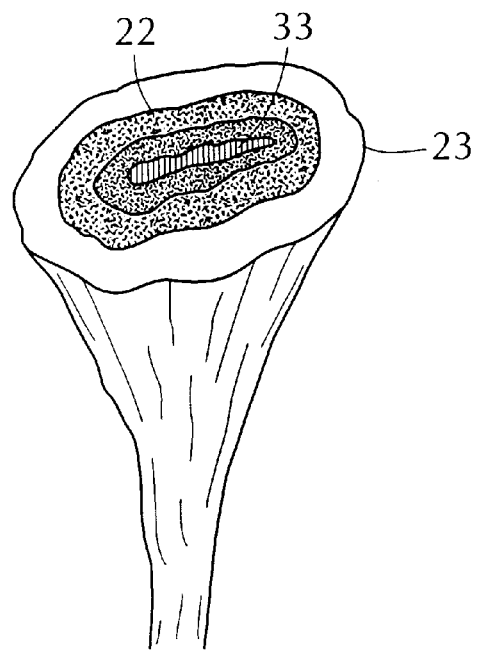
FIG. 12 is a cross sectional illustration of a closed, lesioned fallopian tube.

A mucosa sensor 32 responsive to applied RF energy passing between the two or more bipolar electrodes 29, 30 or 31 determines the condition of the transmural formation of the lesion 22, see FIGS. 4 and 12, between each of the bipolar electrodes 29, 30 and/or 31 to thereby signal the electrosurgical generator 27 during monitoring for controlling the application of RF to the inside wall 33 of the fallopian tube 23. The mucosa sensor 32 is in the preferred embodiment a temperature sensor, see FIG. 1, positioned on the patient end 24 in a space 34 between two or more of the bipolar electrodes 29, 30 and 31 for measuring the change in mucosal layer temperature during the application of RF energy. The RF generator 27 electrically coupled to the two or more bipolar electrodes 29, 30 and 31 and the mucosa sensor 32 would in this approach include a phase detector 35 positioned in the RF generator 27. The phase detector 35 is thus in circuit with the electrical coupling between the RF generator 27 and the two or more bipolar electrodes 29, 30 and 31 for determining reactance of tissue as an indicator of lag or lead of the voltage wave form or current wave form, see FIG. 13, delivered to the patient end 24. The phase detector 35 thereby measures the change in mucosal layer 33 as a tissue effect endpoint during the application of RF energy. The phase detector 35 is shown in FIG. 13 and has two input voltages $V_v$, a 500 kHz waveform proportional to the RF output voltage, and $V_I$, a 500 kHz voltage proportional to the RF current output. Phase detector 35 has a phase lock loop that processes these two signals producing an output voltage ($V_{out}$) proportional to the phase between the two inputs, thus giving the magnitude of the lead or lag of the phase angle between the two waveforms. A change in this phase angle would imply that the capacitive or inductive component of the tissue has changed and this could be a marker that implies that the tissue is sufficiently coagulated. The generator 27 supplying RF energy in a particular embodiment has activation controlled to endpoints of time, impedance, phase, or temperature. Power, current, voltage, temperature rise and steady-state temperature are controlled for producing the desired lesioning effect in the mucosa layer 33. Several cycles are possible wherein multiple endpoints are achieved as milestones for lesion 22 creation. The source of RF can either be a stand-alone generator 27 with a temperature feedback loop in FIG. 3 as thermometry processor 36 or an interface 37 in FIG. 2 as a D to A converter that controls the power into the device from an external source. The interface 37 would then modulate power to have the same effect as the generator 27 with temperature control. A microprocessor 38 in controlling temperature operates over two stages. In the first stage, the baseline temperature is measured and then the slope or intended rise is calculated to achieve the target temperature in 10 seconds. In the second stage, the temperature is held at the target for a second 10 second period. In each stage, proportional control is used to adjust power delivery from the generator 27. The power delivery from the generator 27 is controlled by a digital-to-analog converter 37 from the microprocessor 38 to drive a voltage that is proportional to power from the RF generator 27.

Proportional control is implemented as follows, where
$T_p$=proportioning band (C)
$P_m$=maximum power (W)
T=measured temperature (C)
$T_s$=target or setpoint temperature (C)
P=power level setting to regulate at the target temperature (W)
If $(T_s-T)>0$ then $P=P_m$
otherwise if $(T_s-T)<0$ then $P=0$
otherwise $P=P_m(T_s-T)T_p$ Proportional control can be implemented on the rise or heatup of the mucosa sensor 32 for temperature when elevated toward the target temperature. Proportional control can also be implemented to hold the temperature constant during stage two, the steady state part of the activation.

Alternately the RF generator 27 would be electrically coupled to the two or more bipolar electrodes 29, 30 and 31 with the mucosa sensor 32 monitoring with an impedance responsive circuit at 39 electrically coupled to the RF generator 27 and sensitive to the impedance between the bipolar electrodes 29, 30 and 31 during the application of RF energy. The impedance responsive circuit 39 would thus be in the electrical coupling between the RF generator 27 and the two or more bipolar electrodes 29, 30, and 31. The impedance responsive circuit 39 could receive voltages proportional to RF voltage and current delivered so a calculator in the impedance responsive circuit 39 would find in real time the impedance delivered to the patient end. The impedance calculated in real time thus verifies initial electrode contact with the tissue and thereafter measures changes in mucosal layer impedance between the bipolar electrodes 29, 30 and 31 during the application of RF energy. The calculator includes a memory having an equation for the power delivery with respect to time and a comparator in the calculator to equate power delivered to power required by the equation for closed loop control of the power delivered over elapsed time thus shaping lesion spread and size. The equation in the memory controls power to a range of 5 to 15 watts to reduce sticking and charring to the electrodes in contact with the mucosa layer. Of course, the impedance circuit 39 could be within the generator 27 and the calculator would be within the microprocessor 38.

Figure 7A:
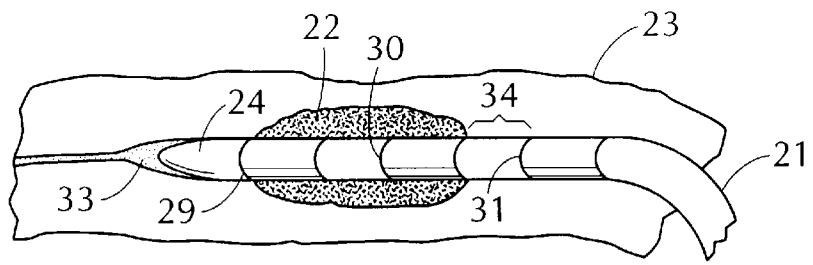
FIG. 7 is a schematic illustration of three electrodes showing the selective bipolar RF activation of certain electrodes to control the lesion location, size, shape and extent.
Figure 7B:
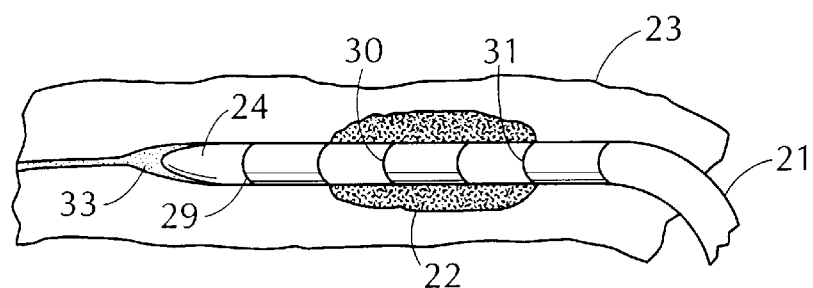
Figure 7C:
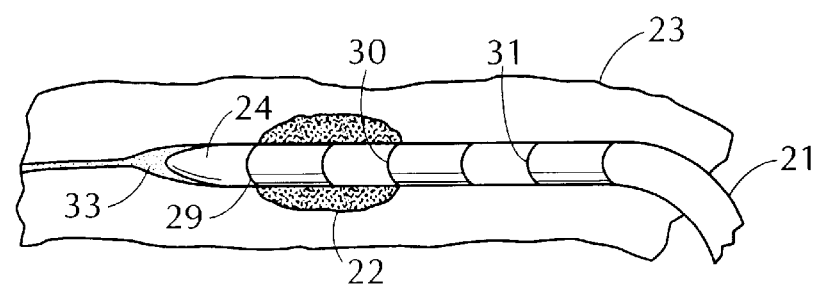

In an alternate embodiment with three bipolar electrodes 29, 30 and 31 shown schematically in FIG. 7, the bipolar electrodes 29, 30 and 31 are connected to RF generator 27 that has switching in a multiplexer 40 shown in FIG. 3 to deliver RF energy selectively between one pair of the bipolar electrodes 29, 30 and 31 or combinations thereof. Thereafter the delivery of RF energy between the various combinations of bipolar electrodes 29, 30 and 31 creates a plurality of lesions therebetween inside the mucosal layer 33 of the fallopian tubes 23 as illustrated in the various combinations shown in FIG. 7. Note that FIG. 7 shows three lesion locations from application of different combinations of bipolar electrodes 29, 30 and 31. Consequently, the size and shape of the respective lesions 22 in each of the three views can be made to order. In the top view of FIG. 7, bipolar electrodes 29 and 30 when activated produce a lesion 22 that begins in the middle thereof between the bipolar electrodes 29 and 30. During second stage of energy delivery, the lesion 22 extends axially in the proximal and distal directions to encompass the bipolar electrodes 29 and 30. Similarly, the centered view of FIG. 7 has the bipolar electrodes 29 and 31 of the same relative polarity and bipolar electrode 30 is the opposite polarity. Thus, the lesion 22 extends from around bipolar electrode 30 to extend symmetrically to the other bipolar electrodes 29 and 31. The bottom view of FIG. 7 has bipolar electrode 29 connected to have one polarity and bipolar electrodes 30 and 31 are the other polarity. The lesion 22 favors geographically the space about bipolar electrode 29 and the gap between bipolar electrodes 29 and 30. Of course this could be shifted distally by reversing the respective polarity and couplings.

The apparatus 20 has the bipolar electrodes 29, 30 and 31 linearly arrayed to be activated in a bipolar fashion as described. Since there may be from two to eight cylindrical electrodes in an array, any combination of two, three, four, etc. electrodes may be chosen to activate. The multiplexer 40 can be used to time sequence the bipolar electrodes 29, 30 and 31 in pairs to provide a contiguous lesion 22 of 1 to 4 cm length. Each lesion can be entirely completed before proceeding to the next combination of bipolar electrodes or they can be time multiplexed such that they are all heating simultaneously. The one or more bipolar electrodes 29, 30 and 31 are spaced apart to create multiple separate lesions 22 inside the fallopian tube 23 without the need to axially relocate the placed catheter 21. The one or more bipolar electrodes 29, 30 or 31 are of different sizes so that when tissue contact is made the position near one of the bipolar electrodes 29, 30 or 31 is defined and the extent, depth and severity of the lesion 22 formation desired by the surgeon results.

Figure 2:
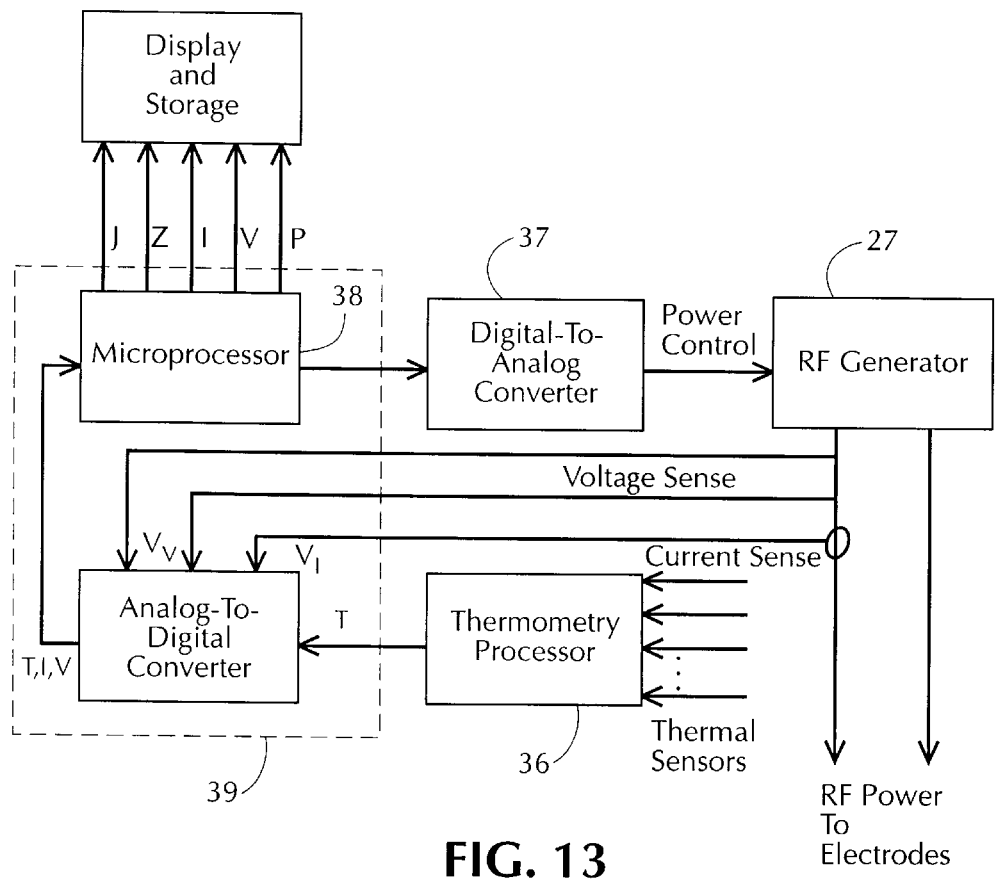
FIG. 2 is a schematic diagram of the circuitry to control the RF energy responsive to thermal feedback.

The catheter 21 is flexible being made of a polymer such as polyethylene and includes a blunt tip at the patient end 24 to facilitate introduction into the fallopian tubes 23 and to avoid perforation thereof. Alternatively, an introducer 41 with a performed bend 42, see FIG. 6, could be placed with its opening 43 directed toward the tubal osteum. In this manner, the RF catheter 21 slides inside the introducer 41 until it enters the fallopian tubes 23. The progression of the catheter 21 entry into the fallopian tube 23 could be monitored by transvaginal or abdominal ultrasound. The mucosa sensor 32 for temperature could be connected to RF generator 27 that has energy delivery control circuitry to regulate delivery of RF energy to a temperature range of about 95 C. to 105 C. between the bipolar electrodes 29, 30 or 31 as illustrated in FIGS. 2 and 3. The energy delivery control circuitry in FIGS. 2 and 3 includes a proportional controller in the microprocessor 38 for substantially regulating the RF energy delivery to control temperature rise time for lesion formation and to maintain the temperature near the mid point of a temperature range of 95 C. to 105 C. during thermal necrosis of tissue for the transmural formation of lesion 22.

A hysteroscope 44 shown schematically in FIG. 5 could visualize the progression of the lesion 22 via video. A hysteroscope 44, made by Wolf Instruments Company located in Minneapolis, Minn., can be used. That device has a miniature crescent shaped outer tube wall that contains imaging delivery and light delivery surrounding an operating channel. The mucosa sensors 32 for temperature as shown in FIG. 1 are located centrally relative to the axis "A" within the gap 34 between adjacent electrodes. The circular cross section of the catheter 21 can be solid with the temperature sensors located centrally of the solid circular cross section of the catheter 21 as seen in the cross section of FIG. 8. The circular cross section of the catheter 21 might be hollow having inside and outside walls 45 and 46, see FIG. 8, of the catheter 21. If a guide wire 47 is used instead of introducer 41 to aid in placement, it would be as shown in FIG. 8. Such temperature sensor 32 is then located on the inside wall 45. The temperature sensors 32 alternatively can be located on the outside wall 46 as in FIG. 9. The temperature sensors 32 alternatively can be located within the wall 48 as in FIG. 11.

A method for transcervical sterilization with thermal energy delivery for creating lesions 22 in the fallopian tubes 23 with steps including transcervically inserting into fallopian tube 23 the catheter 21 elongate along its axis "A" and the catheter 21 with its patient end 24. The catheter 21 is generally circular in cross section and sized for the fallopian tube 23. The step of delivering RF energy and monitoring the effect of RF energy during delivery on the mucosa at the connector on the end of the catheter 21 opposite the patient end 24 is included. Circumscribing the catheter 21 with two or more bipolar electrodes 29, 30 and 31 on the patient end 24 thereof so each of the electrodes is spaced from one another while passing RF energy between the two or more bipolar electrodes 29, 30 and 31 are steps of the method. The step of determining the condition of the transmural formation of lesion 22 between each of the electrodes with the mucosa sensor 32 located between the electrodes is followed during the application of RF energy.

The method step of transcervically inserting into fallopian tube 23 is performed by the surgeon manipulating during transcervical placement and withdrawal the connector 25 shaped and located at the end opposite. The step of determining the condition of the transmural formation of lesion 22 between each of the electrodes in an alternate method includes measuring impedance change during delivery of RF energy. The step of determining the condition of the transmural formation of lesion 22 between each of the electrodes preferably includes measuring temperature change during delivery of RF energy. The step of determining the condition of the transmural formation of lesion 22 between each of the electrodes includes controlling temperature of the mucosa during delivery of RF energy to achieve temperature the range of about 95 C. to 105 C. in the mucosa. The step of controlling temperature of the mucosa during delivery of RF includes forming lesion 22 substantially through the wall of the fallopian tube 23. The step of collapsing the lesioned surface of the fallopian tube 23 after withdrawal of the catheter 21 followed by adhering with a fibroid growth the collapsed adjoining surfaces during a period of three to ten days after withdrawal is preferably followed; this condition is illustrated in FIG. 12.

Figure 14:
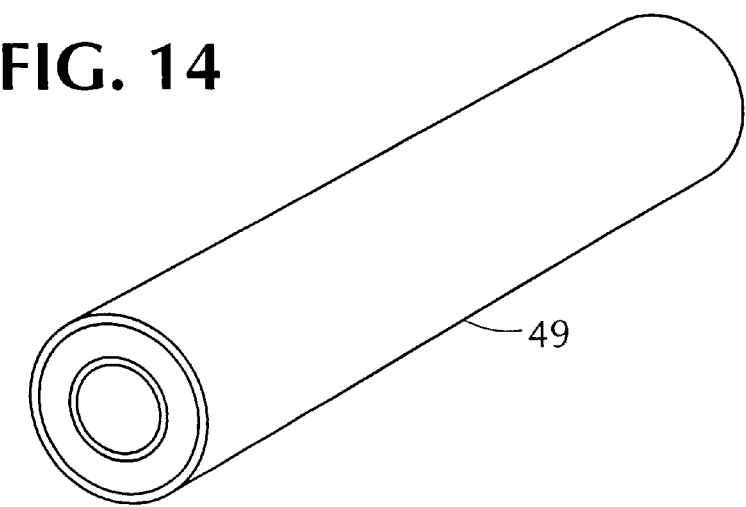
FIG. 14 is a partial perspective view of a piezoelectric element as would be carried by a catheter into the lumen.

Another apparatus for transcervical sterilization with thermal energy delivery for creating lesions 22 in the fallopian tubes 23 has the elongate circular catheter 21 with its patient end 24 sized for transcervical insertion into the fallopian tube 23. One or more piezoelectric transducers 49 in FIG. 14 are on the patient end 24 of the catheter 21. As illustrated in FIG. 14, piezoelectric transducer 49 is a thermal energy source (e.g., C5800 or PZT8, Valpey-Fisher, Framington, Ma.) which transmits an acoustic wave that is absorbed by the adjacent tissue and is converted to heat. Each piezotransducer 49 is a thin cylinder circumscribing the catheter 21. The cylinder is coated on the inside and outside with a thin gold or gold/chromium coating to provide a conductive surface as a pathway to energize the opposing cylindrical faces with an AC voltage in the range of 3–12 MHz. The wall thickness determines the resonant frequency of the driving voltage. The cylinder is preferably located such that its inner cylinder wall rides on the catheter 21. The outside of the cylinder is coated with an insulating coating or is loosely placed inside of an insulator (i.e. polyethylene) that allows cooling fluid to be circulated around the cylinder surface. This coolant reduces the surface temperature of the piezoelectric transducer 49, cools the tissue in contact with the device and provides acoustic coupling. In another embodiment, the PZT element is inside of the catheter 21 and thus acoustically beams through the catheter 21. Electrical leads from a driving generator supply energy to each piezotransducer included to transfer electrical fluctuating energy from the driving generator to each piezotransducer 49. Each piezotransducer 49 is located to heat mucosa 33 tissue. The connector 25 on the end of the catheter 21 opposite the patient end 24 includes separable terminations for the electrical leads for piezoelectric energy and for monitoring. The connector 25 is shaped for the surgeon to manipulate during transcervical placement and withdrawal. The mucosa sensor 32 responds to applied thermal energy passing from the one or more piezotransducers 49 and determines the condition of the transmural formation of a lesion 22 about the one or more piezotransducers 49. The one or more piezotransducers 49 are preferably spaced axially from at least one adjacent piezotransducer 49. Although not shown, this is identical to arrangement of the bipolar electrodes 29, 30 and 31. The preferred tip is blunt and insulated to serve as a guide for the catheter 21.

The current method includes placement of the bipolar electrodes 29, 30 and 31 into the fallopian tube 23. Impedance and temperature are monitored to assure proper placement. Blanching of the fallopian tube 23 wall is visible through scope 44 as the tissue desiccates. The imaging catheter attaches to video to allow observation of the lesion 22 and placement of the bipolar electrodes 29, 30 and 31.

Placement of the apparatus during a rabbit study used the catheter that delivers the RF energy to lesion the fallopian tubes that was flexible and had a slight taper in the tip with a blunt and sealed end to minimize perforation. The transcervical entry was made either with a rigid or flexible hysteroscope with an operating channel of 1–1.5 mm for passage of the electrode. Under direct visualization, markings on the catheter at 10 mm intervals allowed the monitoring of insertion depth to place the lesion in the correct target zone which should be in the cornua or ampulla zone of the fallopian tube.

The bipolar RF electrodes placed into the fallopian tube with intimate contact with the mucosal layer blanches and constricts slightly upon heating the zone of mucosa between the electrodes. The level and rate of energy application reduces sticking of the electrode to the mucosa as well as charring. When sticking was excessive, the electrode did not easily remove. When excessive charring occurred due to high temperatures, the electrodes cause a tunnel and the normally closed tube remained open after the electrode removal. In the range of energy applied resulting in temperatures between 95–105 C., the tube closes after removal of the electrodes and the catheter easily slid out. The depth of the lesion is 1–3 mm of the tubal wall extending outward from the inner lumen and falling off radially such that the outer wall will not become so hot as to harm nearby structures that may include bowel or other heat sensitive organs. FIG. 12 shows the crossection of the fallopian tube. The inner mucosal surfaces are normally closed as shown in the figure. After the lesioning is performed, the mucosal walls will once again close together. The intended extent of the lesion is shown shaded in the figure.

The healing process ultimately closed the treated fallopian tube. The initial response of the heating of the fallopian tube is an inflammatory response that then began to close the tube. Over time, the tissue fibroses and the lumen closes or is obliterated. Thus, no plug or foreign body is left in place in the lesion site. Because the lumen walls do not immediately adhere, removal of the catheter and electrodes is easy. Following the lesion creation, sufficient healing time of 2–4 weeks is required to insure tubal closure. Complete closure is necessary to avoid ectopic pregnancy. The quality of the lesion site may then be evaluated by one of the following methods: 1) an x-ray contrast material injected into the tubal osteum and examined by fluoroscopy, 2) a small laparoscope is placed abdominally or transvaginally into the abdomen to evaluate a colored dye injected into the tubal osteum and observed to exit from the fimbrial end of the tube, or 3) microbubble emulsions are injected into the tubes and color flow doppler or sonography evaluates the extent of the flow down the tube.

Mini-pig Study

In a study of swine with 3 week healing, 105 C. lesions were made at one or both ends of the fallopian tubes. The mucosa of the fallopian tube secrete fluid continuously and thus if both ends are sealed create a large fluid-distended zone called hydrosalpinx. In fallopian tubes with lesions on only one side, there was no hydrosalpinx. In 8/11 tubes with lesions on both ends, hydrosalpinx was evident. In several of the fallopian tubes, the lumen was obliterated as seen in histological analysis.

Rabbit Study

In two mating studies of 70 rabbits, in activations where the bipolar electrodes delivered either 95 or 100 C. to the mucosal layer of the fallopian tube, there were no pregnancies. The healing period was 4 weeks or 3 months after lesioning and mating was daily for three weeks post-healing. The rabbit fallopian tubes are somewhat smaller in diameter than humans, although the lesions were transmural with blanching on the outside of the structure immediately after lesioning. In humans with the larger fallopian tube, the lesions will be somewhat diminished through the wall to the outer layers. The fallopian tubes of the rabbits were given a 95 C. or 105 C. thermal dose with a 10 second rise to the target temperature and then a further 10 second hold. The catheter was immediately removed from the fallopian tube. There was a single electrode failure where the target temperature was reached after 13 seconds and not well maintained at steady-state. The uterine horn associated with this fallopian tube had 7 gestational sacs. In the remaining 19 fallopian tubes that were treated to 95 C. according to protocol, there were no gestational sacs. In the 105 C. series, there were no pregnancies in the 20 uterine horns treated. There were 39 gestational sacs in the 8 control uterine horns.

Procedure in Humans

The device is used with transvaginal and transcervical access. The patient is premedicated with an oral sedative and the cervix is anesthetized with a paracervical block. If dilation is required, this would be done next to allow a $CO_2$ hysteroscope to enter the cervix. The hysteroscope would have an operating channel of at least 1 mm and be either rigid or flexible. The hysteroscope is inserted into the cervix and advanced superiorly towards the fundus. The tubal osteum is then visualized on either right or left side. Then the catheter electrode is advanced a fixed distance (marked on the catheter electrode) until it enters the tubal osteum and enters sufficiently to be placed into the cornual or isthmus region of the fallopian tubes. The $CO_2$ insufflator is turned off, then two or more electrodes are then attached to the output of the generator and the contact impedance read to assure viable tissue contact, especially if concern about tubal perforation is an issue. A temperature sensor which could be a thermocouple, thermistor or fiberoptic probe is located in the catheter between the active electrodes. Power is applied at 500 kHz in two cycles. The target temperature is between 95 C. and 105 C. The electrodes are then energized during cycle 1 which is 10 seconds in duration and power is controlled such that the temperature of the sensor ramps linearly to the target temperature.

In cycle 2, the power is adjusted such that the temperature remains constant over a 10 second cycle. Following this cycle, power is turned off and the temperature decrease is observed as well as impedance values to reassure that the electrodes are still in contact with the tissue inside the fallopian tube. The fallopian tube is a normally closed structure and the energy deposited and lesion created is such that the electrode does not stick to the tube as it is removed and that the tube then assumes its normally closed resting state. Insufflation is resumed. The other tubal osteum is then located, the electrode passed inside and the procedure repeated. As the coagulation process is underway, the hysteroscope allows observation of steam, smoke or popping of the tissue during the time power is applied. Alternately, if difficulty (such as resistance) is encountered during insertion of the catheter, a linear everting catheter sheath may be used to guide introduction and advancement of the catheter electrode into the fallopian tube. A third alternative would be to consider an ultrasound-guided procedure with echogenic, precurved introducer catheters such as the Jansen Andersen insemination set (Cook Instruments). Although this is not feasible for all women due to anatomic variation, the procedure is possible about 75–90% of the time. Adequate placement can be confirmed by abdominal ultrasound. Overall, this procedure can be done much more rapidly than hysteroscopy, and cervical dilatation/anesthesia is not necessary.

For embolization of blood vessels, a transcatheter technique of non-surgical management to occlude affected arteries and prevent further bleeding is done. The vessels would first be imaged by arteriography, CT or MRI to track the cause of hemorrhage or the extent of the anomalous vessel with appropriate feeder vessels to target for occluding. A percutaneous puncture is made and a steerable wire is inserted into the nearest vessel to allow access to the target embolization site. Using common over-the-wire techniques, the thermal embolization catheter as described for tubal ligation, but having an axial passage, is passed to the embolization site. Power is applied preferably with a bipolar configuration as described previously. Temperatures between 50 and 90 C. are controllably reached to create an embolus. The catheter is withdrawn following the heating; thus, forming an autologous thrombus. Angiography is redone to check the vessel for leakage or patency. The patient can be monitored after the procedure with CT or MRI scanning.

Any apparatus internally placed within a vessel for treating it by controlled spaced apart energy delivery from a catheter to ablate, lesion or thrombose tissue about the catheter is the concept. A catheter elongate along an axis has a patient end and is generally circular in cross section and sized for insertion into and passage within the vessel. A connector on the end of the catheter opposite the patient end includes terminations for transmitting energy and for monitoring. The connector is shaped for the surgeon to manipulate during vessel placement and withdrawal. Two or more spaced apart energy delivery members are on the patient end of the catheter. Each of the members is separated axially from another and each of the members circumscribes the catheter. A sensor responds to energy applied to the lining by passing between the two or more members. The sensor determines the amount of ablation or thrombosis or the condition of the formation of a lesion between each of the members. A source of energy electrically couples to the terminations for transmission to the members as the sensor controls the amount of energy delivered to the tissue.

While particular preferred embodiments and methods have been illustrated and described the scope of protection sought is in the claims that follow.

What is claimed is:

1. An apparatus for transcervical sterilization with a controlled bipolar RF catheter for creating thermal lesions in the fallopian tubes, the apparatus comprising:

a catheter elongate along an axis thereof and with a patient end, the catheter being generally circular in cross section and sized for transcervical insertion into the fallopian tube;

a connector on an end of the catheter opposite the patient end, the connector including terminations for RF and monitoring, the connector being shaped for the surgeon to manipulate during transcervical placement and withdrawal;

two or more bipolar electrodes on the patient end of the catheter, each of the electrodes being spaced from one another, each of the electrodes circumscribing the catheter; and a mucosa sensor responsive to applied RF energy passing between the two or more bipolar electrodes, the mucosa sensor for determining transmural formation of a lesion between each of the electrodes, wherein energy delivery control circuitry connected to receive signals of transmural formation from the mucosal sensor includes a proportional controller for substantially regulating the RF energy delivery to control temperature rise time for lesion formation and to maintain the temperature near a mid point of a range during thermal necrosis of tissue for transmural formation of a lesion.

2. The apparatus for transcervical sterilization according to claim 1 wherein the mucosa sensor is a temperature sensor positioned on the patient end in the space between the two or more bipolar electrodes for measuring the change in mucosal layer temperature during the application of RF energy.

3. The apparatus for transcervical sterilization according to claim 2 wherein the temperature sensor is connected to an RF generator, the RF generator including the energy delivery control circuitry to regulate delivery to a range of about 95 C. to 105 C.

4. The apparatus for transcervical sterilization according to claim 2 wherein the temperature sensor is located centrally relative to the axis within the space between adjacent electrodes.

5. The apparatus for transcervical sterilization according to claim 4 wherein the circular cross section of the catheter is solid and the temperature sensor is located at the center of the solid circular cross section of the catheter.

6. The apparatus for transcervical sterilization of claim 5 wherein the circular cross section of the catheter is hollow having an inside and a outside wall of the catheter.

7. The apparatus for transcervical sterilization according to claim 6 wherein the temperature sensor is located on the inside wall.

8. The apparatus for transcervical sterilization according to claim 6 wherein the temperature sensor is located on the outside wall.

9. The apparatus for transcervical sterilization according to claim 1 wherein an RF generator is electrically coupled to the two or more bipolar electrodes and the mucosa sensor is a phase detector positioned in the RF generator, the phase detector in circuit with the electrical coupling between the RF generator and the two or more bipolar electrodes for determining reactance of tissue as an indicator of lag or lead of the voltage wave form or current wave form delivered to the patient end for measuring the change in mucosal layer as a tissue effect endpoint during the application of RF energy.

10. The apparatus for transcervical sterilization according to claim 1 wherein an RF generator is electrically coupled to the two or more bipolar electrodes and the mucosa sensor is an impedance responsive circuit positioned in the RF generator, the impedance responsive circuit in the electrical coupling between the RF generator and the two or more bipolar electrodes for determining voltage and current delivered and a calculator in the impedance responsive circuit for finding impedance delivered to the patient end for finding initial electrode contact with the tissue and for measuring mucosal layer change during the application of RF energy.

11. The apparatus for transcervical sterilization according to claim 10 wherein the calculator includes a memory including an equation for power delivery with respect to time and a comparator in the calculator to compare power delivered to power required by the equation for closed loop control of the power delivered over elapsed time to shape lesion spread and shape.

12. The apparatus for transcervical sterilization according to claim 11 wherein the two or more bipolar electrodes are spaced apart to create multiple separate lesions inside the fallopian tube without moving the placed catheter.

13. The apparatus for transcervical sterilization of claim 11 wherein the equation in the memory controls power to reduce sticking and charring to the electrode of tissue in contact therewith.

14. The apparatus for transcervical sterilization according to claim 1 wherein there are three electrodes connected to an RF generator to deliver RF energy selectively between adjacent electrodes at one time to create a plurality of lesions therebetween inside the fallopian tubes' mucosal layer.

15. The apparatus for transcervical sterilization according to claim 1 wherein the catheter is flexible and includes a blunt tip at the patient end to facilitate introduction into the fallopian tubes and to avoid preformation thereof.

16. The apparatus for transcervical sterilization according to claim 1 wherein a videoscope surrounds the transcervically inserted catheter for the visualization of the progression of the lesion via video.

17. The apparatus for transcervical sterilization according to claim 1 wherein the two or more electrodes are of different size.

18. A method for transcervical sterilization with thermal energy delivery for creating lesions in the fallopian tubes with two or more bipolar electrodes on a catheter, the steps comprising:

transcervically inserting into a fallopian tube a catheter elongate along an axis thereof and with a patient end, the catheter generally circular in cross section and sized for the fallopian tube;

delivering RF from a connector on an end of the catheter opposite the patient end and monitoring the effect of RF on mucosa;

circumscribing the catheter with the two or more bipolar electrodes on the patient end of the catheter, each of the electrodes spaced from one another;

passing RF energy between the two or more bipolar electrodes;

determining the condition of the transmural formation of a lesion between each of the electrodes with a mucosa sensor located between and being spaced from adjacent electrodes; and providing energy delivery control circuitry to receive signals of transmural formation from the mucosal sensor, the energy delivery control circuitry including a proportional controller for substantially regulating the RF energy delivery to control temperature rise time for lesion formation and to maintain the temperature near the midpoint of a range during thermal necrosis of tissue for transmural formation of a lesion.

19. The method for transcervical sterilization with thermal energy delivery for creating lesions in the fallopian tubes according to claim 18 wherein the step of transcervically inserting into a fallopian tube is performed by manipulating the end opposite the patient end during transcervical placement and withdrawal.

20. The method for transcervical sterilization with thermal energy delivery for creating lesions in the fallopian tubes according to claim 18 wherein the step of determining the condition of the transmural formation of a lesion between each of the electrodes includes measuring impedance change during delivery of RF.

21. The method for transcervical sterilization with thermal energy delivery for creating lesions in the fallopian tubes according to claim 18 wherein the step of determining the condition of the transmural formation of a lesion between each of the electrodes includes measuring temperature change during delivery of RF.

22. The method for transcervical sterilization with thermal energy delivery for creating lesions in the fallopian tubes according to claim 21 wherein the step of determining the condition of the transmural formation of a lesion between each of the electrodes includes controlling temperature of the mucosa during delivery of RF to the range of about 95 C. to 105 C.

23. The method for transcervical sterilization with thermal energy delivery for creating lesions in the fallopian tubes according to claim 22 wherein the step of controlling temperature of the mucosa during delivery of RF includes formation of a lesion substantially through the wall of the fallopian tube.

24. The method for transcervical sterilization with thermal energy delivery for creating lesions in the fallopian tubes according to claim 23 further including the step of collapsing the lesioned surface of the fallopian tube after withdrawal of the catheter followed by adhering with a fibroid growth the collapsed adjoining surfaces during a period of three to ten days after withdrawal.

* * * * *